United States Patent [19]

Lannert

[11] 4,100,358
[45] Jul. 11, 1978

[54] KETAL POLYCARBOXYLATE COMPOUNDS

[75] Inventor: Kent P. Lannert, Freeburg, Ill.

[73] Assignee: Monsanto Company, St. Louis, Mo.

[21] Appl. No.: 736,962

[22] Filed: Oct. 29, 1976

[51] Int. Cl.² ............................................. C07C 59/22
[52] U.S. Cl. ..................... 560/180; 252/89 R;
252/99; 252/132; 252/135; 252/546; 252/548;
252/550; 252/89 B; 252/551; 252/554;
252/555; 252/558; 252/DIG. 11; 260/501.15;
260/501.17
[58] Field of Search ............... 260/535 P, 484 P; 560/180

[56] References Cited

U.S. PATENT DOCUMENTS

| 3,935,257 | 1/1976 | Ruest .................................... 560/180 |
| 3,970,698 | 7/1976 | Lannert ................................. 560/180 |

*Primary Examiner*—Paul J. Killos
*Attorney, Agent, or Firm*—S. M. Tarter; E. P. Grattan; F. D. Shearin

[57] ABSTRACT

This disclosure concerns:
(a) Compounds having the molecular structure represented by the formula:

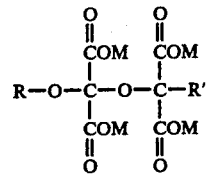

wherein M is selected from the group consisting of —H, —CH$_3$, —C$_2$H$_5$, —NH$_4$, —Na, —K and combinations thereof; R is selected from the group consisting of an alkyl radical (branched or straight chain) containing up to about C$_{20}$, —CH(CO$_2$M)$_2$, and —CH$_2$CO$_2$M, and R' is selected from the group consisting of an alkyl radical (branched or straight chain) containing up to about C$_{20}$, —H, and —OR;
(b) a method for making the compounds of (a);
(c) solid and liquid detergent compositions comprising compounds of (a), and
(d) washing processes employing the compounds of (a) and/or the compositions of (c).

9 Claims, No Drawings

KETAL POLYCARBOXYLATE COMPOUNDS

BACKGROUND OF THE INVENTION

The invention relates to ketal polycarboxylate compounds, methods for preparing such compounds, liquid and solid detergent formulations comprising them, the use of the compounds as detergent builders, metal chelants and thresholding agents, and the use of the detergent compositions containing such compounds in washing processes.

The compounds have utility in complexing various metal ions, including alkaline earth metal ions, such as calcium ions which contribute to hardness in water. In combination with detergent compounds and compositions, the compounds are useful in improving the cleaning ability of the detergents. Thus, the primary areas of utility for the compounds are in water treatment, e.g., for water softening and as detergency builders and threshold agents.

DESCRIPTION OF THE PRIOR ART

In my U.S. Pat. No. 3,704,320 issued Nov. 28, 1972, there are disclosed compounds which may generally be described as ether carboxylates and which are disclosed to have utility as detergent builders or the like. The chemical structures and specific properties of the ether carboxylates described in the referenced patent are significantly different from the compounds of this invention.

SUMMARY OF THE INVENTION

The invention relates to ketal polycarboxylates, methods for making such compounds, compositions employing such compounds, and methods for employing the compounds and compositions containing them.

The compounds have the following general formula:

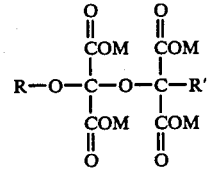

wherein M is selected from the group consisting of —H, —CH$_3$, —C$_2$H$_5$, —NH$_4$, —Na, —K, and combinations thereof; R is selected from the group consisting of an alkyl radical (branched or straight chain) containing up to about C$_{20}$, —CH(CO$_2$M)$_2$, and —CH$_2$CO$_2$M, and R' is selected from the group consisting of an alkyl radical (branched or straight chain) containing up to about C$_{20}$, —H, and —OR.

The general method for making the compounds of the invention may be illustrated as follows:

(A) A compound of the general formula:

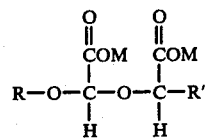

wherein R is selected from the group consisting of —CH$_3$ and —C$_2$H$_5$, and M is as described above, is reacted with LiN(ipr)$_2$ and then with CO$_2$ to produce a compound of the general formula:

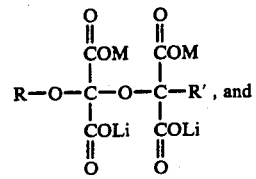

(B) reacting the product compound of Step (A) with H$^+$ in the presence of an alcohol to produce the subject compounds ester forms.

The salt forms of the compounds may then be formed by (a) reacting the compounds produced in Step (B) with NaOH or KOH, or (b) by directly reacting the product of Step (A) with NaOH or KOH.

The reactions discussed in Paragraphs (A) - (B) above may be schematically illustrated as follows:

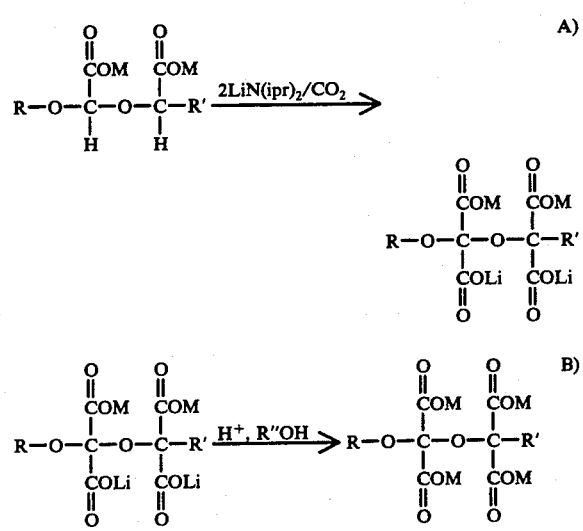

wherein R" is a lower alkyl group.

The reactions for conversion of the compounds to the salt form may be schematically illustrated as follows:

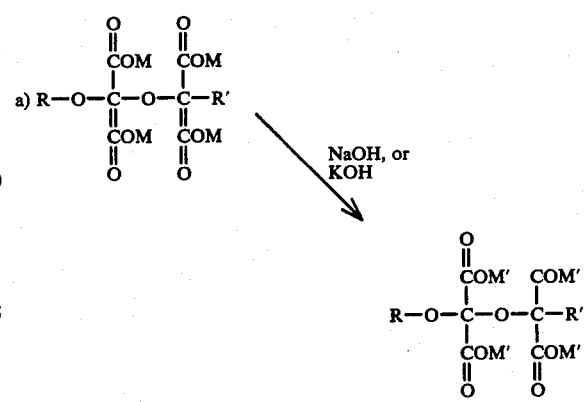

-continued $$\text{b) } R-O-\underset{\underset{\underset{O}{\parallel}}{\underset{COLi}{|}}}{\overset{\overset{\overset{O}{\parallel}}{COM}}{C}}-O-\underset{\underset{\underset{O}{\parallel}}{\underset{COLi}{|}}}{\overset{\overset{\overset{O}{\parallel}}{COM}}{C}}-R' \xrightarrow{\text{NaOH or KOH}}$$

wherein M is —$CH_3$ or —$C_2H_5$, and where M' is —Na or —K.

The compositions of the invention comprise various standard solid or liquid detergent compositions containing an amount of the above described compounds or mixtures of such compounds sufficient to enhance the cleaning capacity of the detergent by providing a building, threshold or other function.

Methods for using the compounds of the invention comprise:

(1) softening water by contacting hard water with the compounds of the invention in an amount and for a time sufficient to remove, usually by chelating or sequestering, certain metal ions present in the water, or to complex ions so that they are not available to interfere with soap or detergent compositions added to the water;

(2) washing soiled articles by contacting the articles with detergent compositions containing or used in the presence of one or more of the compounds of the invention, the compounds being used in amounts sufficient to build or otherwise enhance the cleaning action of the detergent compositions.

DETAILED DESCRIPTION OF THE INVENTION

A. Compounds

The compounds of the invention have the molecular structure represented by the following formula:

$$R-O-\underset{\underset{\underset{O}{\parallel}}{\underset{COM}{|}}}{\overset{\overset{\overset{O}{\parallel}}{COM}}{C}}-O-\underset{\underset{\underset{O}{\parallel}}{\underset{COM}{|}}}{\overset{\overset{\overset{O}{\parallel}}{COM}}{C}}-R'$$

wherein M, R and R' are as described above.

B. Methods for Synthesizing the Compounds

In my earlier work on the synthesis of other ether carboxylates, I successfully utilized a Williamson ether synthesis to produce the desired compounds. This synthesis, while probably adequate to produce small yields of the compounds of the invention, does not appear adequate to produce larger, commercial scale yields. Therefore, I developed a new process for producing the compounds.

My new process comprises first preparing as a starting material a halogenated dialkyl glycolate, e.g., chlorinated dimethyl diglycolate, by reacting dialkyl diglycolate with halogen as follows:

$$\underset{(I)}{H-\underset{\underset{H}{|}}{\overset{\overset{O}{\parallel}}{\overset{COM}{|}}}{C}}-O-\underset{\underset{H}{|}}{\overset{\overset{O}{\parallel}}{\overset{COM}{|}}}{C}}-H + X_2 \longrightarrow \underset{(II)}{X-\underset{\underset{H}{|}}{\overset{\overset{O}{\parallel}}{\overset{COM}{|}}}{C}}-O-\underset{\underset{H}{|}}{\overset{\overset{O}{\parallel}}{\overset{COM}{|}}}{C}}-H$$

wherein M is alkyl, preferably lower alkyl, e.g., methyl or ethyl, and X is halogen, preferably chlorine (Cl).

The halogenated alkyl diglycolate (II) is then reacted with an alkali metal alkoxide, e.g., sodium methoxide as follows:

$$(II) + AOR \longrightarrow \underset{(III)}{RO\underset{\underset{H}{|}}{\overset{\overset{O}{\parallel}}{\overset{COM}{|}}}{C}}-O-\underset{\underset{H}{|}}{\overset{\overset{O}{\parallel}}{\overset{COM}{|}}}{C}}-H$$

wherein A is alkali metal and M is as described above.

Next, Compound III was reacted with lithium diisopropyl amide as follows:

$$\underset{(III)}{RO\underset{\underset{H}{|}}{\overset{\overset{O}{\parallel}}{\overset{COM}{|}}}{C}}-O-\underset{\underset{H}{|}}{\overset{\overset{O}{\parallel}}{\overset{COM}{|}}}{C}}-H} \xrightarrow{LiN(ipr)_2} \underset{(IV)}{RO\underset{\underset{Li}{|}}{\overset{\overset{O}{\parallel}}{\overset{COM}{|}}}{C}}-O-\underset{\underset{Li}{|}}{\overset{\overset{O}{\parallel}}{\overset{C-OM}{|}}}{CH}}$$

Compound IV was then reacted with $CO_2$ as follows:

$$(IV) + CO_2 \longrightarrow \underset{(V)}{RO\underset{\underset{\underset{O}{\parallel}}{\underset{COLi}{|}}}{\overset{\overset{\overset{O}{\parallel}}{COM}}{C}}-O-\underset{\underset{\underset{O}{\parallel}}{\underset{COLi}{|}}}{\overset{\overset{\overset{O}{\parallel}}{COM}}{C}}}{CH}}$$

Compound V may then be converted to the acid, ester or salt form of the compounds of the invention. To produce a half ester-half acid form of the compounds of the invention Compound V is reacted with an ion exchange material to produce $$\underset{(VI)}{RO\underset{\underset{\underset{O}{\parallel}}{\underset{COH}{|}}}{\overset{\overset{\overset{O}{\parallel}}{COM}}{C}}-O-\underset{\underset{\underset{O}{\parallel}}{\underset{COH}{|}}}{\overset{\overset{\overset{O}{\parallel}}{COM}}{C}}}{CH}}$$

wherein R and M are as described above.

The ester form of the compounds may then be produced by reacting Compound VI with acid/alkanol as follows:

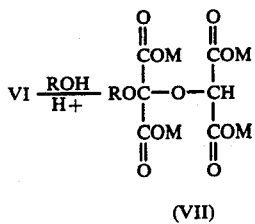

(VII)

wherein R and M are as described above.

The alkali metal salt forms of the compounds may then be produced by hydrolysis of the ester form VII as by reaction with an alkali metal hydroxide as follows:

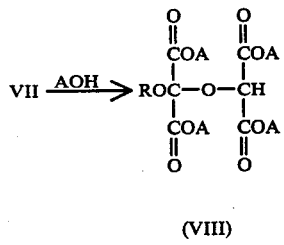

(VIII)

wherein A is alkali metal and R is as described above.

The ammonium salt form may then be produced by exchange of the sodium with ammonium by well known ion-exchange procedures.

The preferred starting material for the synthesis of the subject compounds, dimethyl chlorodiglycolate, may be prepared in accordance with a previously known procedure which comprises the chlorination of dimethyl diglycolate.

In detergency builder applications, the use of the alkali metal salts of the compounds, particularly the sodium salt, is preferred. However, in some formulations (such as liquid formulations where greater builder solubility is required) the use of ammonium or alkanol ammonium salts may be desirable.

The detergent formulations will contain at least 1% by weight and preferably at least 5% by weight of the salt forms of compounds of this invention. In order to obtain the maximum advantages of the builder compositions of this invention the use of from 5% to 75% of these salts is particularly preferred. The salt compounds of this invention can be the sole detergency builder or these compounds can be utilized in combination with other detergency builders which may constitute from 0 to 95% by weight of the total builders in the formulation. By way of example, builders which can be employed in combination with the novel salt compounds of this invention include water soluble inorganic builder salts, such as alkali metal polyphosphates, i.e., the tripolyphosphates and pyrophosphates, alkali metal carbonates, borates, bicarbonates and silicates and water soluble organic builders, including amino polycarboxylic acids and salts such as alkali metal nitrilotriacetates, cycloalkane polycarboxylic acids and salts, ether polycarboxylates, alkyl polycarboxylates, epoxy polycarboxylates, tetrahydrofuran polycarboxylates such as 2,3,4,5 or 2,2,5,5 tetrahydrofuran tetracarboxylates, benzene polycarboxylates, oxidized starches, amino (trimethylene phosphonic acid) and its salts, diphosphonic acids and salts (e.g., methylene diphosphonic acid; 1-hydroxy ethylidene diphosphonic acid) and the like.

The detergent formulations will generally contain from 5% to 95% by weight total builder (although greater or lesser quantities may be employed if desired) which, as indicated above, may be solely the builder salt compounds of this invention or mixtures of such compounds with other builders. The total amount of builder employed will be dependent on the intended use of the detergent formulation, other ingredients of the formulation, pH conditions and the like. For example, general laundry powder formulations will usually contain 20% to 60% builder; liquid dishwashing formulations 11% to 12% builder; machine dishwashing formulations 60% to 90% builder. Optimum levels of builder content as well as optimum mixtures of builders of this invention with other builders for various uses can be determined by routine tests in accordance with conventional detergent formulation practice.

The detergent formulations will generally contain a water soluble detergent surfactant although the surfactant ingredient may be omitted from machine dishwashing formulations. Any water soluble anionic, nonionic, zwitterionic or amphoteric surfactant can be employed.

Examples of suitable anionic surfactants include soaps such as the salts of fatty acids containing about 9 to 20 carbon atoms, e.g., salts of fatty acids derived from coconut oil and tallow; alkyl benzene sulfonates-particularly linear alkyl benzene sulfonates in which the alkyl group contains from 10 to 16 carbon atoms; alcohol sulfates; ethoxylated alcohol sulfates; hydroxy alkyl sulfonates; alkenyl and alkyl sulfates and sulfonates; monoglyceride sulfates; acid condensates of fatty acid chlorides with hydroxy alkyl sulfonates and the like.

Examples of suitable nonionic surfactants include alkylene oxide (e.g., ethylene oxide) condensates of mono and polyhydroxy alcohols, alkyl phenols, fatty acid amines, and fatty amines; amine oxides, sugar derivatives such as sucrose monopalmitate; long chain tertiary phosphine oxides, dialkyl sulfoxides; fatty acid amides, (e.g., mono or diethanol amides of fatty acids containing 10 to 18 carbon atoms), and the like.

Examples of suitable zwitterionic surfactants include derivatives of aliphatic quaternary ammonium compounds such as 3-(N,N-dimethyl-N-hexadecyl ammonio)propane-1-sulfonate and 3-(N,N-dimethyl-N-hexadecyl ammonio)-2-hydroxy propane-1-sulfonate.

Examples of suitable amphoteric surfactants include betains, sulfobetains and fatty acid imidazole carboxylates and sulfonates.

It will be understood that the above examples of surfactants are by no means comprehensive and that numerous other surfactants are known to those skilled in the art. It will be further understood that the choice and use of surfactants will be in accordance with well understood practices of detergent formulation. For example, anionic surfactants, particularly linear alkyl benzene sulfonate are preferred for use in general laundry formulations, whereas low foaming nonionic surfactants are preferred for use in machine dishwashing formulations.

The quantity of surfactant employed in the detergent formulations will depend on the surfactant chosen and the end use of the formulation. In general, the formulations will contain from 5% to 50% surfactant by weight, although as much as 95% or more surfactant may be employed if desired. For example, general laundry powder formulations normally contain 5% to 50%, preferably 15% to 25% surfactant; machine dishwashing formulations 0.5% to 5%; liquid dishwashing formulations 20% to 45%. The weight ratio of surfactant to builder will generally be in the range of from 1:12 to 2:1.

In addition to builder and surfactant components, detergent formulations may contain fillers such as sodium sulfate and minor amounts of bleaches, dyes, optical brighteners, soil anti-redeposition agents, perfumes and the like.

In machine dishwashing compositions the surfactant will be a low-foaming anionic or preferably, nonionic surfactant which will constitute 0 to 5% of the formulation.

The term "low-foaming" surfactant connotes a surfactant which, in the foaming test described below, reduces the revolutions of the washer jet-spray arm during the wash and rinse cycles less than 15%, preferably less than 10%.

In the foaming test, 1.5 grams of surfactant is added to a 1969 Kitchen-Aid Home Dishwasher, Model No. KOS-16, manufactured by Hobart Manufacturing Company which is provided with means for counting revolutions of the washer jet-spray arm during wash and rinse cycles. The machine is operated using distilled water feed at a machine entrance temperature of 40° C. The number of revolutions of the jet-spray arm during the wash and rinse cycles is counted. The results are compared with those obtained by operation of the machine using no surfactant charge and the percentage decrease in the number of revolutions is determined.

The surfactant should, of course, be compatible with the chlorine containing component hereinafter discussed. Examples of suitable nonionic surfactants include ethoxylated alkyl phenols, ethoxylated alcohols (both mono- and di-hydroxy alcohols), polyoxyalkylene glycols, aliphatic polyethers and the like. The widely commercially utilized condensates of polyoxypropylene glycols having molecular weight of from about 1400 to 2200 with ethylene oxide (the ethylene oxide constituting 5 to 35 weight percent of the condensate) are, for example, advantageously used in the machine dishwashing formulations of this invention.

Suitable low-foaming anionic surfactants include alkyl diphenyl ether sulfonates such as sodium dodecyl diphenyl ether disulfonates and alkyl naphthalene sulfonates.

Mixtures of suitable low-foaming surfactants can be utilized if desired.

In addition, machine dishwashing formulations will contain sufficient chlorine providing compound to provide 0.5% to 2% available chlorine. For example, the formulation may contain from 0.5% to 5%, preferably 1% to 3% of a chlorocyanurate or from 10% to 30% chlorinated trisodium phosphate. Suitable chlorocyanurates are sodium and potassium dichlorocyanurate; [(monotrichloro) tetra-(monopotassium dichloro)] penta-isocyanurate; (monotrichloro) (monopotassium dichloro) diisocyanurate.

Machine dishwashing compositions should additionally contain from 5% to 30% soluble sodium silicate having an SiO$_2$ to Na$_2$O mole ratio of from 1:1 to 3.2:1 preferably about 2.4:1 to inhibit corrosion of metal parts of dishwashing machines and provide over-glaze protection to fine china.

Machine dishwashing compositions will generally contain at least 10%, preferably at least 20% builder, up to a maximum of about 90% builder. The new salt compounds of this invention should constitute at least 5% of the weight of the machine dishwashing formulation.

The invention is further illustrated by the following examples wherein all parts and percentages are by weight unless otherwise indicated.

EXAMPLE 1

A stirred reactor was charged with 156 g dimethyl diglycolate and 300 ml benzene. The reactor was purged with N$_2$ for several minutes while the material in the reactor was cooled to about 5° C. Cl$_2$ flow was then begun and the reactor was irradiated with a sun lamp to photo-stimulate the reaction. The temperature was maintained at about 15° C., by circulating ice water through a coil in the reactor. Cl$_2$ flow was continued for about 45 minutes. The reaction mixture was then purged with N$_2$. The reaction mixture was filtered and stripped of benzene by evaporation. The reaction mixture was further cooled and filtered and the filtrate was vacuum distilled. The product was dimethyl chlorodiglycolate.

To a solution of sodium methoxide (NaOMe) in methanol there was added a solution of the dimethyl chlorodiglycolate in methanol, the temperature being maintained at about 15° C. Additional NaOMe solution was added until the structure solution was slightly basic. The reaction mixture was stripped of solvent and dissolved in a mixture of a 75% aqueous NaHCO$_3$ solution and ether. The layers were separated and the aqueous layer was extracted with ether. The extracts and original ether layer were combined, washed with water and saturated NaCl solution. The solution was then dried over CaSO$_4$ and roto-evaporated. The residue was vacuum distilled and again vacuum distilled at 90°–100° C., at 0.05 mm Hg. A yield of about 70 g of quite pure compound was obtained and the structure was confirmed by $^1$Hnmr to be dimethyl methoxydiglycolate of the structure

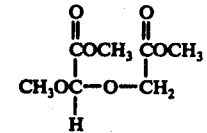

Next, 56 ml of diisopropylamine in 450 ml of tetrahydrofuran (THF), maintained at a temperature below about −20° C., was added to 250 ml of 1.6M n-butyl lithium. The mixture was allowed to warm slowly to 10° C., and then was cooled to −75° C. 33.8 of the previously prepared dimethyl methoxy diglycolate in about 20 ml THF was then added at a rate such that the temperature could be maintained below −70° C. The mixture turned a dark red-brown as the dimethyl methoxy diglycolate was added. After 10 minutes at −70° to 75° C., a rapid stream of CO$_2$ was introduced. After about one hour at −75° C., the CO$_2$ stream was slowed so as just to maintain a CO$_2$ blanket. (The temperature rose to about −60° C., during the initial CO$_2$ introduction). After standing overnight, the solvent was removed from the reaction mixture by roto-evaporation. The residue obtained was dissolved in water and passed through an H$^+$ ion exchange column. The aqueous effluent was roto-evaporated leaving a viscous red-brown oil. This product is the half ester of the structure

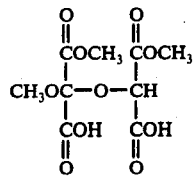

The half ester was then converted to the tetramethyl ester by esterification with 300 ml of methanol containing 15 ml of acetyl chloride with stirring at ambient conditions. The resulting reaction mixture was then neutralized with $Na_2CO_3$, filtered and roto-evaporated to strip methanol. The residue was diluted with water and extracted with ether and ethylacetate:acetone. The extract was washed with water, dried and roto-evaporated. About 11 g of red-brown residue was obtained which, upon gas-liquid chromatographic analysis, proved to be about 44% of the tetramethyl ester of the compounds of the invention having the following structure:

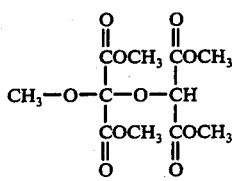

Pure compound was recovered by using a Kugel-Rohr with a bath temperature of 255° C., to separate the volatile portion from the high boilers (about half of the crude product). The volatile fraction was then vacuum distilled and the product crystallized from the fractions collected between 142° and 156° C. Recrystallization from ethanol gave 4 g (4% yield) of white crystalline powder with a melting point of 48°-52° C. 'Hnmr and C,H,O analysis confirmed the above structure.

EXAMPLE 2

To a solution of 85 ml of a 0.5N NaOH solution at room temperature there was added 3.0 g of the tetramethyl ester prepared as described in Example 1. The solution was allowed to stand for two days at room temperature with a stream of $N_2$ blowing across the surface to reduce the volume. A thick syrup was obtained which solidified after working up under methanol. The solid was ground in a blender under methanol, collected on a filter, washed with methanol, acetone and ether and dried in a vacuum oven at 60°-80° C., for 2-3 hours. The product, 3.3 g of powder gave 'Hnmr consistent with the structure of the sodium salt of the tetramethyl ester.

EXAMPLE 3

The tetrasodium salt compound was tested for detergency building capacity by the Divalent Electrode Test Procedure as described by E. A. Matzner et al in an article entitled "Organic Builder Salts as Replacements for Sodium Tripolyphosphate(I)" published in TENSIDE, Vol. 10, 1973, Nos. 3 and 5, pages 119-125 and 239-245.

The divalent electrode titration test gave values of $a = 62$ mV, $b = 36$ mV, $c = 7.5$ ml and $d = 9.4$ ml for an intensity capacity index of 79% of the index for sodium tripolyphosphate (STP), indicating that the compounds will serve as useful replacements for STP in detergent compositions and washing applications where non-phosphorus containing materials are desired.

The tetrasodium salt form of the compound having the formula

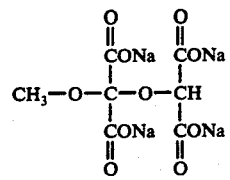

was subjected to biodegradation testing with natural sewage according to a standard biodegradation test. Two samples were tested, one showing acclimatization in about four weeks and the second in about three weeks. This result was good since biodegradability is an important property being sought in detergent compositions apt to be introduced into the nation's waterways. This result was also unexpected based upon the high resistance to biodegradation of the structurally closely related compound

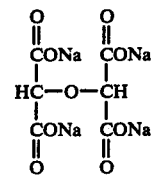

The invention will be understood by those skilled in the art not to be limited to the specifically described embodiments, but to encompass compounds, compositions and processes within the scope of the following claims.

The embodiments of the invention in which an exclusive property or privilege is claimed are defined as follows:

1. Compounds of the molecular structure represented by the formula:

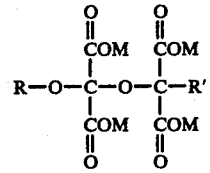

wherein M is selected from the group consisting of —H, —$CH_3$, —$C_2H_5$, —$NH_4$, —Na, —K and combinations thereof; R is selected from the group consisting of an alkyl radical (branched or straight chain) containing up to about $C_{20}$, —$CH(CO_2M)_2$, and —$CH_2CO_2M$, and R' is selected from the group consisting of an alkyl radical (branched or straight chain) containing up to about $C_{20}$, —H, and —OR.

2. The compounds of claim 1 wherein R is an alkyl radical, each M is —$CH_3$ and R' is H.

3. The compound of claim 1 wherein R is —$CH_3$, each M is —$CH_3$ and R' is H.

4. The compound of claim 1 wherein R is —$C_2H_5$, each M is —$C_2H_5$ and R' is H.

5. The compound of claim 1 wherein R is —$CH_3$, each M is Na and R' is H.

6. The compound of claim 1 wherein R is —$C_2H_5$, each M is Na and R' is H.

7. The compound of claim 1 wherein R is —$CH_3$, each M is H and R' is H.

8. The compound of claim 1 wherein R is —$C_2H_5$, each M is H and R' is H.

9. The compound of claim 1 wherein R is —$CH_3$, the two upper M's are —$CH_3$ or —$C_2H_5$, the two lower M's are H and R' is H.

* * * * *